(12) United States Patent
Bartenbach et al.

(10) Patent No.: US 7,956,228 B2
(45) Date of Patent: Jun. 7, 2011

(54) METHOD AND DEVICE FOR PRODUCING ACETYLENE AND SYNTHESIS GAS BY RAPIDLY MIXING THE REACTANTS

(75) Inventors: Bernd Bartenbach, Limburgerhof (DE); Kai Rainer Ehrhardt, Speyer (DE); Arne Hoffmann, Mannheim (DE); Frank Kleine Jaeger, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 754 days.

(21) Appl. No.: 11/910,996

(22) PCT Filed: Apr. 21, 2006

(86) PCT No.: PCT/EP2006/061768
§ 371 (c)(1),
(2), (4) Date: Oct. 9, 2007

(87) PCT Pub. No.: WO2006/114399
PCT Pub. Date: Nov. 2, 2006

(65) Prior Publication Data
US 2008/0188698 A1    Aug. 7, 2008

(30) Foreign Application Priority Data

Apr. 23, 2005 (DE) .......................... 10 2005 018 981

(51) Int. Cl.
*C07C 4/04* (2006.01)
*B01J 8/00* (2006.01)

(52) U.S. Cl. ........ 585/534; 585/536; 585/538; 585/539; 585/540; 252/373; 48/127.9; 48/198; 48/216

(58) Field of Classification Search .................. 585/534, 585/537, 539, 540, 536, 538; 252/373; 48/127.9, 48/198, 216
See application file for complete search history.

(56) References Cited

U.S. PATENT DOCUMENTS

| 5,789,644 A | 8/1998 | Paessler et al. |
|---|---|---|
| 6,365,792 B1 * | 4/2002 | Stapf et al. .................... 585/539 |
| 2004/0151663 A1 | 8/2004 | Nougier et al. |
| 2004/0205996 A1 | 10/2004 | Bartenbach et al. |

FOREIGN PATENT DOCUMENTS

| EP | 0 287 380 | 10/1988 |
|---|---|---|
| GB | 794 157 | 4/1958 |
| GB | 2 099 843 | 12/1982 |

* cited by examiner

*Primary Examiner* — Prem C Singh
(74) *Attorney, Agent, or Firm* — Oblon, Spivak, McClelland, Maier & Neustadt, L.L.P.

(57) ABSTRACT

A process for the preparation of acetylene and synthesis gas by partial thermal oxidation in a reactor which has a burner having passages, wherein the starting materials to be reacted are rapidly and completely mixed only immediately before the flame reaction zone in the passages of the burner, a mean flow rate which exceeds the flame propagation velocities under the given reaction conditions being established in the mixing zone within the passages.

10 Claims, 1 Drawing Sheet

United States Patent US 7,956,228 B2

METHOD AND DEVICE FOR PRODUCING ACETYLENE AND SYNTHESIS GAS BY RAPIDLY MIXING THE REACTANTS

CROSS-REFERENCE TO RELATED APPLICATIONS

The present application is a 35 U.S.C. §371 National Stage patent application of International patent application PCT/EP06/061768, filed on Apr. 21, 2006, which claims priority to German patent application DE 102005018981.4, filed on Apr. 23, 2005.

The present invention relates to an improved process for the preparation of acetylene and synthesis gas by partial thermal oxidation in a reactor which has a burner having passages, and to an apparatus for carrying out the process according to the invention.

The mixer/burner/fire space/quench combinations usually used for the BASF-Sachsse-Bartholoméacetylene process—designated below simply as "reactor" when the combination is referred to—are referred to, for example, in German Patent 875 198.

The acetylene burners used on the present production scale are distinguished by their cylindrical geometry of the fire space (reactor). The starting materials are premixed via a diffuser and fed, substantially without back-mixing, to the burner block, which preferably has hexagonally arranged passages. In one embodiment, for example, 127 bores of 27 mm internal diameter are arranged hexagonally on a circular base cross section having a diameter of about 500 mm. The downstream fire space in which the flame of the acetylene-forming partial oxidation reaction is stabilized likewise has a cylindrical cross section and corresponds in appearance to that of a short pipe (of, for example, 533 mm diameter and 400 mm length). The entire burner comprising burner block and fire space is suspended from the top into a quench container of larger cross section, via a flange. At the height of the exit level from the fire space, quenched nozzles are installed on one or more quench distributor rings, outside the circumference of said fire space, which quench nozzles atomize the quench medium, e.g. water or oil, with or without the aid of an atomizing medium and spray said quench medium approximately perpendicularly to the main direction of flow of the reaction gases leaving the fire space. This direct quench has the function of cooling the reacting stream extremely rapidly so that subsequent reactions, i.e. in particular the degradation of acetylene formed, are frozen. The range and distribution of the quench jets is ideally such that as homogeneous a temperature distribution as possible is achieved in as short a time as possible.

Since the starting materials (hydrocarbons or oxygen) are preheated and premixed in the BASF-Sachsse-Bartholome acetylene process and similar partial thermal oxidations, this gives rise to the danger of pre-ignition and re-ignition owing to the limited thermal stability of the mixtures, including thermal stability limited with regard to time. The consequences are generally known, and shutdowns and flare activity with risks of emission may result, particularly in the case of relatively high proportions of reactive starting components, such as hydrogen or liquefied gas (LPG). However, it is precisely the use of these starting components that is desirable since they can permit increases in yield and/or in capacity.

In the known processes, the premixing of the starting materials is effected in the mixing diffuser in a relatively large volume and at high temperatures. Owing to an increased proportion of reactive starting components, catalytically active particles and surfaces, e.g. rust, coke, etc., of large residence time distributions, for example through back-mixing zones and fluid flow stagnation points, the induction times for the ignition of the mixture may be exceeded, with the result that the cost-efficiency and effectiveness of the process are impaired. Furthermore, the introduction of additional apparatuses, such as, for example, ignition burners, proves to be scarcely feasible since, owing to the flow disturbances arising thereby, it is also to be feared that the induction times for the ignition of the mixture will be exceeded.

BRIEF SUMMARY OF INVENTION

It was therefore the object to provide an improved process for the preparation of acetylene and synthesis gas, which avoids said disadvantages and which furthermore permits higher preheating temperatures and the use of higher pressures. This process should be capable of being realized easily and economically, and it should also be carried out simply with existing, conventional burners.

BRIEF DESCRIPTION OF THE DRAWING

The figure shows a schematic diagram of the burner.

Accordingly, a process for the preparation of acetylene and synthesis gas by partial thermal oxidation in a reactor which has a burner having passages was found, wherein the starting materials to be reacted are rapidly and completely mixed only immediately before the flame reaction zone in the passages of the burner, a mean flow rate which exceeds the flame propagation velocities under the given reaction conditions being established in the mixing zone within the passages. Furthermore, an apparatus for carrying out the process according to the invention was found.

Figure 1:
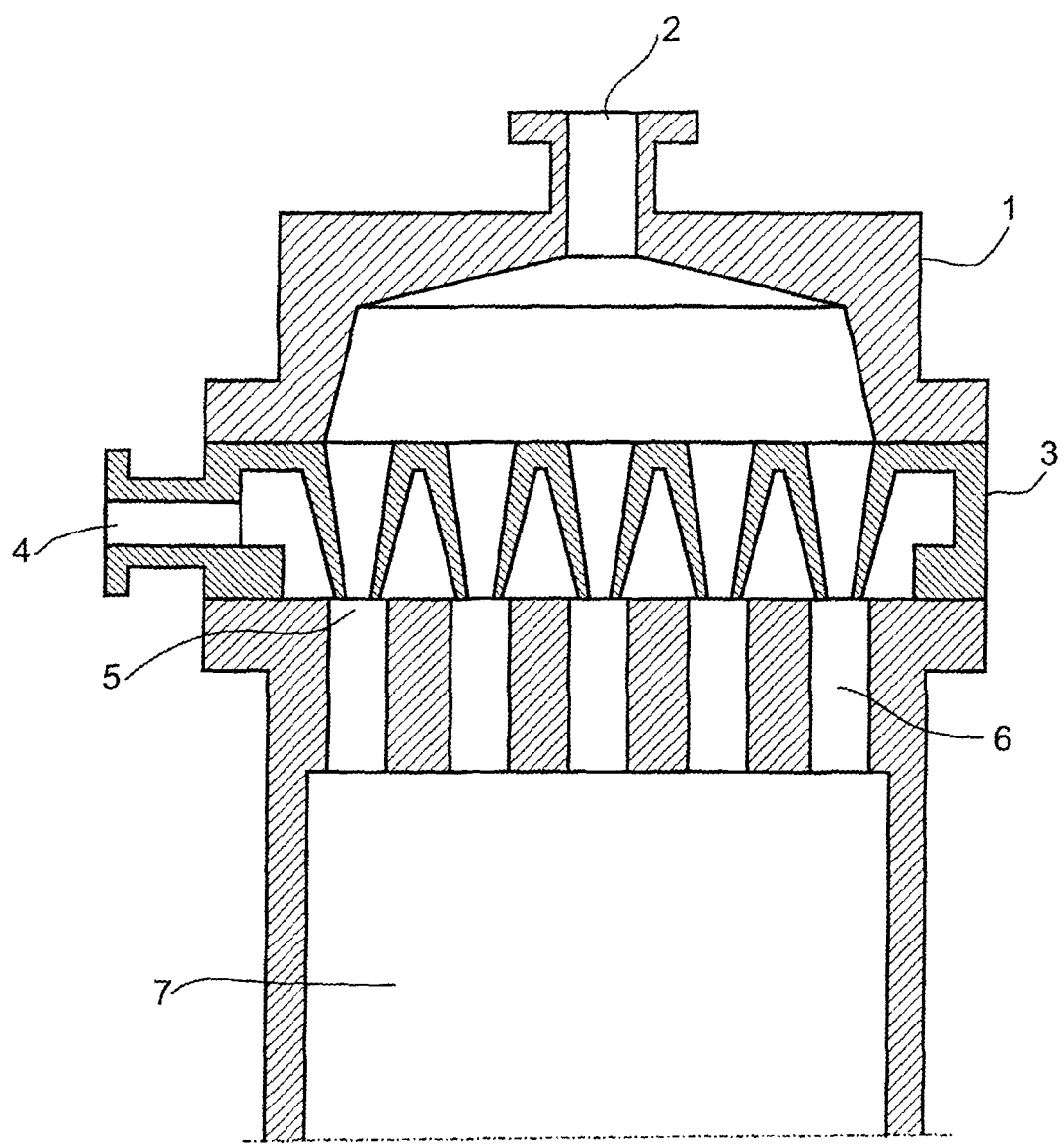

The undesired pre-ignitions and re-ignitions described can be avoided according to the invention if the premixing of the starting materials is not carried out, as has been customary to date, in a large volume (in the mixing diffuser) at fairly low flow rates, but this premixing is advantageously transferred to the large number of burner block bores ("passages") which in any case are typically present. The passages generally have the function of stabilizing the flame in a locally defined manner. By means of the measure according to the invention, the mixing is divided into many small volumes, and a forward flow which has a high velocity develops in the passages. In the highly turbulent flow present there, the mixing can be established easily and rapidly by suitable mixing geometries, at the same time strike-back of the flame due to the much higher flow rate in the passages than the flame velocity being avoided. The design of the mixing geometries can be easily determined by the person skilled in the art with a knowledge of this invention. For example, mixing nozzles which operate according to the Venturi principle or the principle of the static mixing tube are suitable for this purpose. A division of the premixing task offers easy transferability and applicability also in the case of the conventional scaling methods for acetylene burners and acetylene reactors.

The burners of the BASF-Sachsse-Bartholome acetylene process are usually water-cooled cylindrical blocks which have a multiplicity of likewise cylindrical bores. Owing to the barriers forming thereby, the stabilization of the flame is supported so that an ideally level flame develops in the fire space above the burner plate. The number of bores and the diameter and spacing thereof are chosen for a given burner capacity in such a way that the flow rate in the bores is above the strike-back velocity but below a critical blow-off velocity.

According to the invention, the mixing of the starting materials is effected only immediately before the flame reaction zone in the passages and not, as to date, in a diffuser. The volume of a burner used on the production scale is about 0.6 m³, whereas the volume of a mixing element according to the invention is about 3 orders of magnitude smaller.

This makes it possible to reduce the residence times in the mixing element to 0.001-0.005 s, whereas they are 0.1-0.3 s in the case of the conventional mixing via the individual diffuser. It is thus possible to premix reaction mixtures whose ignition lag time is in the millisecond range. The mixing element is characterized by substantially back-mixing-free and rapid mixing of the two starting materials with the minimization of the resulting pressure drop. By appropriate design, the admission pressure of one of the two starting materials for intake and mixing according to the principle of a static mixing tube can also be used.

An apparatus suitable for carrying out the process according to the invention can be particularly easily and advantageously realized by retrofitting existing burners by means of an intermediate flange for separate starting material feed. In an embodiment one or more ignition burners which ignite a main reaction within the burner are introduced into a diffuser which is upstream of the burner. Here, one of the two starting materials is fed via the premixing diffuser used to date, while the respective other starting material is distributed via the intermediate flange over the individual mixing elements. If one of the two starting materials is present at elevated pressure, the introduction of this substance can be effected by cross-jets. If the two starting materials have virtually the same admission pressure, that with the higher admission pressure is preferably fed via the premixing diffuser used to date, so that the mixing tube operates according to the principle of the static mixer. The function of the mixing tube is performed here by the passages of the existing burner block, so that this remains slightly adapted in its function. In both realization variants, shutdowns, flare activities and associated emissions can be avoided by the measure, and there are new possibilities for using or recycling crude synthesis gas, (crude) hydrogen or relatively high proportions (>10% by volume) of ethane, ethylene or liquefied gases (propane, butane, etc.) and for increasing the preheating temperatures to above 600° C. and the reactor pressure to above 1.3 bar, which would otherwise give rise to pre-ignitions. It is thus possible to realize either increases in yield or increases in throughput in the existing processes. For the recycling of hydrogen or hydrogen-containing crude synthesis gases which are obtained as byproducts and coupled products in all acetylene processes operated on an industrial scale, there is the advantage of their preferred oxidation owing to the higher reactivity of the hydrogen compared with the frequently customary starting material methane (from natural gas). Thus, in the partial oxidation processes, the heat-releasing oxidation reaction is steered toward the hydrogen which is unsuitable as an acetylene precursor, and the carbon source of the acetylene formation, i.e. the feedstock hydrocarbon, is protected. The path leading to acetylene formation tends to have a pyrolytic character and uses crack reactions of the feedstock hydrocarbon, which are induced by this in situ heat release.

The apparatus according to the invention is explained in more detail by way of example with reference to the figure. The latter shows a burner (1) into which one starting material is fed via a pipe (2). The second starting material is passed in via the apparatus part (3) inserted by means of an intermediate flange, via a pipe (4). The two starting materials are mixed by a mixer (5), which is not shown in detail, in the passages (6) of the burner, immediately before entry into the combustion chamber (7).

The invention can be applied to all partial oxidation acetylene processes, but in particular to the BASF acetylene process and its various embodiments. A combination with the processes disclosed in the Patent Applications DE 103 13 527 A1, DE 103 13 528 A1 and DE 103 13 529 A1 is also expressly advantageous and is herewith incorporated by reference.

The invention differs expressly from processes in which the premixing is effected in the reactor, combustion chamber or fire space in a diffusion flame, with turbulent diffusive mixing processes taking place at the same time and side by side with the combustion reaction, as disclosed, for example, in DE 20 52 543 C3, especially since it completely avoids the disadvantages stated there with respect to a shift of the yield of acetylene to higher proportions of ethylene. Moreover, it should be emphasized that the retrofittability of existing plants and processes by means of a simple apparatus and hence their transformation to the process according to the invention can be regarded as being particularly advantageous.

Suitable starting materials are in principle all hydrocarbons customary for acetylene and/or synthesis gas preparation, such as, for example, methane, higher saturated or unsaturated hydrocarbons and biofuels which are present in gaseous form at the chosen preheating temperature.

The process principle according to the invention can also be used for other processes for acetylene and synthesis gas preparation with said advantages.

The process according to the invention permits economical preparation of acetylene and synthesis gas in high yields. The time for premixing of the two reactants is substantially reduced, so that high preheating temperatures or pressures of the starting materials and higher proportions of reactive starting components can be realized without pre-ignitions taking place in the mixing space, with the result that the effectiveness of the process is further increased.

An additional advantage of the process according to the invention is that the installation of flow-disturbing parts is no longer prohibited in the region of the diffuser, which effects the mixing and feed of the mixture to the burner block in the case of the conventional burners, since the local residence time of the gas which is increased in the region of separation vortices can no longer induce pre-ignitions. Thus, internals, such as ignition burners, which were not customary to date in acetylene burners, alternative flame monitoring systems, measuring probes or cooling water feeds, for example for supplying burner types according to DE 103 13 528 A1, can now advantageously be realized. The process can advantageously also be realized in existing burners by simple conversion in an economical manner and with little process engineering effort.

EXAMPLES

1. In the operation of a conventional 25 metric tons per day acetylene burner, typically product gas compositions which comprise 8.5% by volume of acetylene are achieved with the use of natural gas.
2. In a second experiment, a feedstock gas which comprises 6% by volume of ethane in addition to natural gas is reacted according to the invention. As a result, the concentrations of acetylene can be increased to 9% by volume in the crack gas.
3. If the ethane content is increased to above 20% by volume, there is an enormous increase in pre-ignitions and the associated flare activities owing to the substantially shorter ignition lag time, so that economical operation of a conventional plant is no longer possible. With the aid of the process according to the invention, these re-ignitions can be avoided, and the acetylene concentration in the crack gas can be increased to above 9.5% of acetylene, which means a further increase in yield.

We claim:

1. A process for the preparation of acetylene and synthesis gas by partial thermal oxidation in a reactor comprising a burner having passages, wherein the process comprises rapid and complete mixing of starting materials, to be reacted in a flame reaction zone, in a mixing zone located within the passages of the burner only immediately prior to entry into the flame reaction zone, wherein a mean flow rate, which exceeds flame propagation velocities, is established within the mixing zone, and
   wherein at least one starting material and another starting material are fed separately to the burner such that their respective streams cross in the mixing zone.

2. The process according to claim 1, wherein one or more ignition burners which ignite a main reaction within the burner are introduced into a diffuser which is upstream of the burner and through which one of the starting materials is fed to the burner.

3. The process according to claim 1, wherein byproduct streams leaving the reactor are recycled to the reactor and mixed with a hydrocarbon before entry into the burner.

4. The process according to claim 3, wherein the recycled byproduct stream is further mixed will oxygen before entry into the burner.

5. The process according to claim 1, wherein hydrocarbon mixtures, other than natural gas, comprised in said starting materials, are mixed, in proportions of more than 10% by volume, with a natural gas before entry into the burner.

6. The process according to claim 1, wherein hydrocarbon mixtures, other than natural gas, comprised in said starting materials, are selected from methane, ethane, ethylene, propane, and butane.

7. The process according to claim 3, wherein the byproduct streams leaving the reactor comprise hydrogen.

8. The process according to claim 5, wherein hydrocarbon mixtures, other than natural gas, are mixed, in proportions of more than 20% by volume, with natural gas before entry into the burner.

9. The process according to claim 5, wherein hydrocarbon mixtures, other than natural gas, are mixed before entry into a preheater for preheating the starting materials upstream of the burner.

10. The process according to claim 9, wherein hydrocarbon mixtures, other than natural gas, arc selected from liquefied gas, saturated hydrocarbons, and unsaturated hydrocarbons, which are gaseous at preheating temperatures of the preheater.

\* \* \* \* \*